(12) United States Patent
Niedospial, Jr.

(10) Patent No.: US 6,213,985 B1
(45) Date of Patent: Apr. 10, 2001

(54) TAPERED SYRINGE BARREL WITH TAPERED PLUNGER

(75) Inventor: John J. Niedospial, Jr., Burlington, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 0 days.

(21) Appl. No.: 09/588,520

(22) Filed: Jun. 6, 2000

(51) Int. Cl.[7] ..................................................... A61M 5/13
(52) U.S. Cl. ............................................. 604/218; 604/187
(58) Field of Search ..................................... 604/181, 182, 604/187, 218, 219, 220, 230; D24/112

(56) References Cited

U.S. PATENT DOCUMENTS

| | | |
|---|---|---|
| 562,425 * | 6/1896 | Scheerer ................................ 604/181 |
| 4,303,070 | 12/1981 | Ichikawa et al. . |
| 4,852,768 * | 8/1989 | Bartsch ................................. 604/220 |
| 4,952,209 * | 8/1990 | Muhlbauer ........................... 604/218 |
| 5,540,660 | 7/1996 | Jenson . |
| 5,735,825 | 4/1998 | Stevens et al. . |
| 5,782,803 * | 7/1998 | Jentzen ................................. 604/110 |

* cited by examiner

*Primary Examiner*—Sharon Kennedy
(74) *Attorney, Agent, or Firm*—Imre Balogh

(57) ABSTRACT

A syringe for injecting a medical fluid into a site or withdrawing a medical fluid from a site, having a syringe barrel and an elastomeric plunger. The syringe barrel is of polymeric material having an inner surface defining a tapered cylindrical chamber extending from the proximal end to the distal end of the syringe. The distal end terminates in a tip, having a bore therethrough, to which an injection needle or a connector is attached. The proximal end receives the slidably insertable elastomeric plunger for reciprocating movement in the tapered cylindrical chamber. The elastomeric plunger is tapered from its proximal end to its distal end. The angle of taper in both the cylindrical chamber and in the elastomeric plunger is at least 1/8°.

11 Claims, 7 Drawing Sheets

TAPERED SYRINGE BARREL WITH TAPERED PLUNGER

BACKGROUND OF THE INVENTION

1. Field of the Invention

This invention relates to a plastic tapered syringe barrel and an elastomeric tapered plunger combination for containing and dispensing a medical fluid from the syringe.

2. Reported Developments

Syringes and cartridges made of glass or polymeric material for delivery of fluids to and from a patient have been proposed and utilized by the prior art, and have achieved a highly developed state. Various requirements related to specific delivery systems have also been addressed. While specific requirements of fluid delivery to and from a patient may vary, means of delivery remain essentially the same and may be characterized by the following general description of a syringe.

A syringe comprises:
  a) a cylindrical barrel having a proximal end designed for receiving a plunger with or without a plunger rod removably attached to the plunger or being integral with the plunger, and a distal end adapted to mount a needle or luer connector thereon; and
  b) a plunger slidably mounted in the barrel.

The plunger is inserted into the barrel at the proximal end of the syringe and thus when fluid is contained in the barrel it may be expelled by pushing the plunger in the barrel towards its distal end; or when the syringe is used to withdraw fluid from a patient, the plunger located at the distal end of the barrel is pulled towards the proximal end of the syringe thereby drawing fluid into the barrel. Since a fluid-tight seal is necessary between the plunger and the inside wall of the barrel, a resilient rubber tip is positioned on the distal end of the plunger, or typically, the plunger is made of resilient rubber-like material. In some of the syringes of the prior art the rubber tip has been replaced with a generally flat, circular disk as part of the plunger.

In order to assure air-tight seal between the inside wall of the syringe barrel and the plunger, prior art plungers are manufactured with a larger outside diameter than the inside diameter of the syringe barrels. When the plunger is introduced into the syringe barrel, it is sufficiently compressed to provide adequate pressure between the inside wall of the syringe and the plunger to seal the interface and withstand the challenges of filling, injecting and withdrawing fluids using the syringe without leakage.

In addition to a leakage-proof seal, another requirement in the syringe/plunger combination is the chemical stability of both the syringe and the plunger. While syringes being made of glass or thermoplastic materials are sufficiently chemically inert to pharmaceutical and biological fluids contained therein, the plungers made of natural rubber or butyl rubber have some undesirable properties. The rubber contains additional chemical components such as fillers and accelerators introduced during the curing process which tend to exude to the surface of the plunger during the contact between the plunger and the fluid contained in the syringe. Such exudate is undesirable in an injection or when a biological fluid, such as blood, is withdrawn from a patient for testing purposes. The problem is further aggravated when there is a long-term storage of the content of the pharmaceutical/biological fluid in the syringe. Recognizing the problem of contamination caused by exudates from plungers made of rubber, the prior art has provided plungers made of thermoplastic materials which do not contain the additives that rubber plungers contain. However, thermoplastic materials are not as resilient as rubbers and the seals formed between thermoplastic plungers and the inside walls of syringes tend to be inadequate in some circumstances. Also, over a period of time on storage the thermoplastic plunger may achieve a compression stage wherein the outside diameter of the plunger is reduced thereby no longer capable of forming a tight seal between it and the inside wall of the syringe.

In addition to the tendency of leakage, the thermoplastic plunger does not slide smoothly in the syringe barrel and requires the exertion of excessive force on the plunger rod to move the plunger in the barrel. The exertion of excessive force on the plunger rod may result in uneven delivery of the fluid to the patient or insertion of the needle into a vein or tissue area to an undesirable depth.

In both the rubber and thermoplastic plungers a relatively large compressive force must be exerted on the plungers by the syringe barrel to provide for a tight, leakproof seal. This quality of the seal, however, makes the movement of the plunger difficult. To remedy the problem the prior art used lubricants to reduce friction and drag between the plunger and the inside surface of the syringe barrel. The use of such lubricants, however, is also undesirable with certain parenteral fluids which tend to disperse or dissolve in the parenteral fluids thereby contaminating the parenteral fluids. Attempts to avoid the use of lubricants included the use of various plunger configurations, such as plungers that were provided with one or more ribs projecting forwardly or rearwardly in the barrel to reduce the frictional drag between the plunger and the inside surface of the barrel.

While fluid tightness and sliding property have improved with these attempts, it appears that improvement in one of these properties is not quite achieved without corresponding decrease in the other property: increasing fluid tightness tends to result in decreasing sliding property, while increasing sliding property tends to result in decreasing fluid tightness.

The present invention is directed to improve the balance between fluid tightness and sliding property in a syringe and, in addition, provides a manufacturing advantage in making the syringe barrel.

SUMMARY OF THE INVENTION

The present invention provides a syringe for medical use designed for injecting a fluid into a site or withdrawing a fluid from a site comprising:

(a) a syringe barrel of polymeric material having a proximal end, a distal end, and an inner surface defining a tapered cylindrical chamber between the proximal end and the distal end for retaining a fluid therein,
  the distal end terminates in a tip having a bore therethrough to which an injection needle or a connector equipped with tubing conduit can be attached; and a proximal end for receiving a plunger;

(b) a plunger comprising: a rigid plunger rod tip having a proximal end, a distal end, a tapered body extending from the proximal end to the distal end; and an elastomeric member mounted on and at least partially covering the plunger rod tip.

The tapered cylindrical chamber has a taper of at least $\frac{1}{8}°$ or more and/or a taper of at least 0.020" variation from the proximal end to the distal end.

Preferably, the plunger profile matches the profile of the tapered cylindrical chamber of the syringe barrel, i.e., having a taper of at least $\frac{1}{8}°$ and/or a taper of at least 0.020" variation from the proximal end to the distal end of the plunger.

The present invention is also directed to the reduction of breakaway and running forces in using the syringe when injecting a fluid from the barrel into a site. Such reduction of the forces facilitates starting and advancing the plunger from the proximal end toward the distal end of the barrel. To achieve this object of the present invention preferred elastomers having a core set of no more than 20% are used for fabricating the elastomeric member covering the plunger rod tip. Core set is defined as the reduction in size of an elastomer that is caused by compressing the elastomer 50% over a period of 24 hours at 120° C. Preferably, the core set in the present invention is no more than about 20%. Most preferred elastomers have a core set between 10% to 15%. Such elastomers include butyl rubbers, polyisoprene, EPDM and natural rubbers.

DETAILED DESCRIPTION OF THE INVENTION

The present invention is directed to syringes and cartridges used to deliver fluids into a site, such as liquid pharmaceutical compositions and diagnostic contrast media delivered into a mammalian patient subcutaneously, intramuscularly or intravenously depending upon the particular medication to be administered. The barrel of the syringe is made of polymeric materials and is equipped with a needle or luer connector having a tubing conduit attached thereto at the distal end thereof through which the fluids are delivered into the desired site. The syringes or cartridges may be pre-filled and sterilized ready for use, or they may be filled from a container, such as a vial, just prior to use. They may be used manually or in connection with power injectors well-known in the art.

The syringes or cartridges of the present invention may also be used to withdraw biological fluids from a patient, such as blood or tissue, for testing or other medical purposes.

The design of the thermoplastic plunger rod tip and the elastomeric plunger assembly used in the syringe or cartridge results in the following desirable characteristics:
reduction of breakaway forces;
reduction of running forces; and
insuring against leakage.

The invention will now be described in reference to syringes, however, it is to be noted that the invention encompasses cartridges as well.

Figure 1:
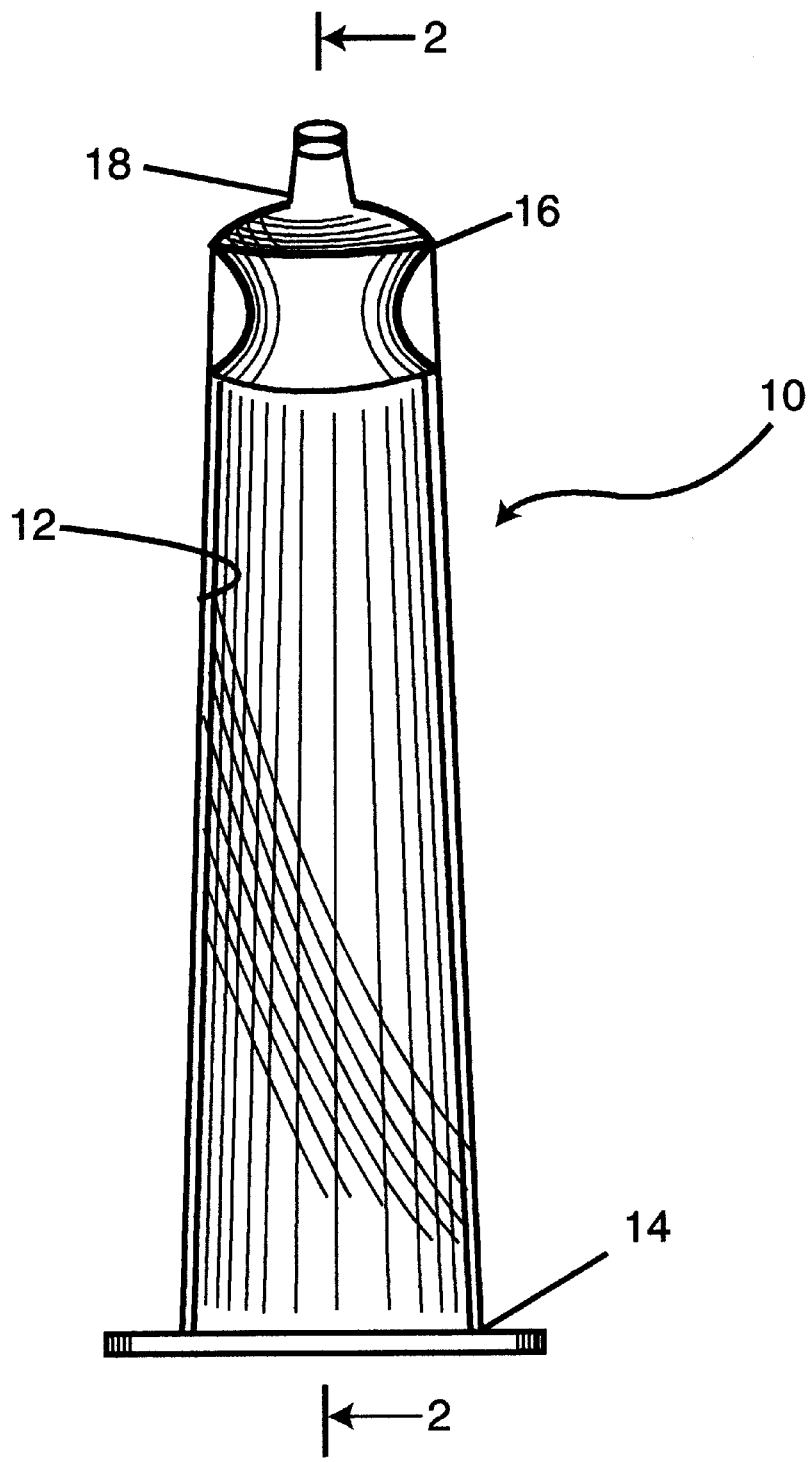
FIG. 1 is a perspective view of the tapered syringe barrel and the tapered plunger positioned in the tapered syringe barrel according to the present invention.
Figure 2:
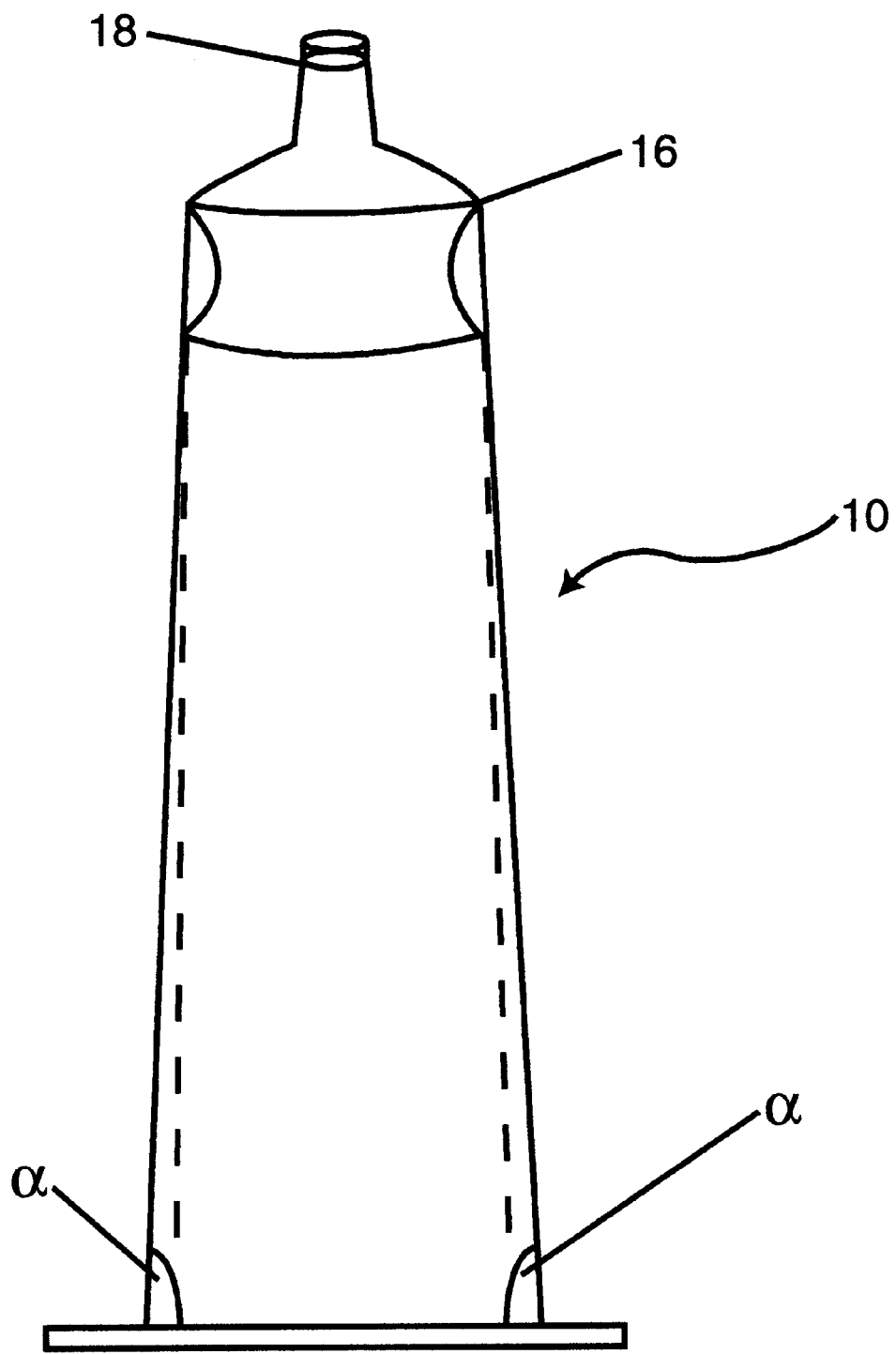
FIG. 2 is a longitudinal cross-sectional view thereof taken along the line 2—2 of FIG. 1.

Referring to the drawings, FIG. 1 shows a perspective view of the tapered syringe barrel and the tapered plunger positioned in the syringe barrel, while FIG. 2 shows a longitudinal cross-sectional view thereof.

The syringe barrel generally designated by the numeral 10 comprises:
an open proximal end 14 which is to receive a plunger;
a distal end 16;
a tip 18 at the distal end having a bore therethrough;
an inside wall 12 enclosing a tapered cylindrical chamber, the tapered cylindrical chamber extending from the proximal end to the distal end of the syringe barrel and is adapted to receive a medical fluid therein; and
an outside wall of the tapered chamber 20 providing the required thickness of the syringe barrel.

The syringe barrel 10 is made of an inert gas-impermeable, substantially transparent material, such as of polyethylene, polypropylene, polycarbonate, polymethylpentene, cyclic olefin copolymers, polystyrene, acrylic polymers and methacrylic polymers.

The tapered cylindrical chamber has a taper designated by $\alpha$ of at least $\frac{1}{8}°$ or more, and preferably of about $\frac{1}{4}°$, or defined with other parameters; a taper having at least 0.020", and preferably of about 0.040" variation from the proximal end to the distal end of the plunger.

Figure 3:
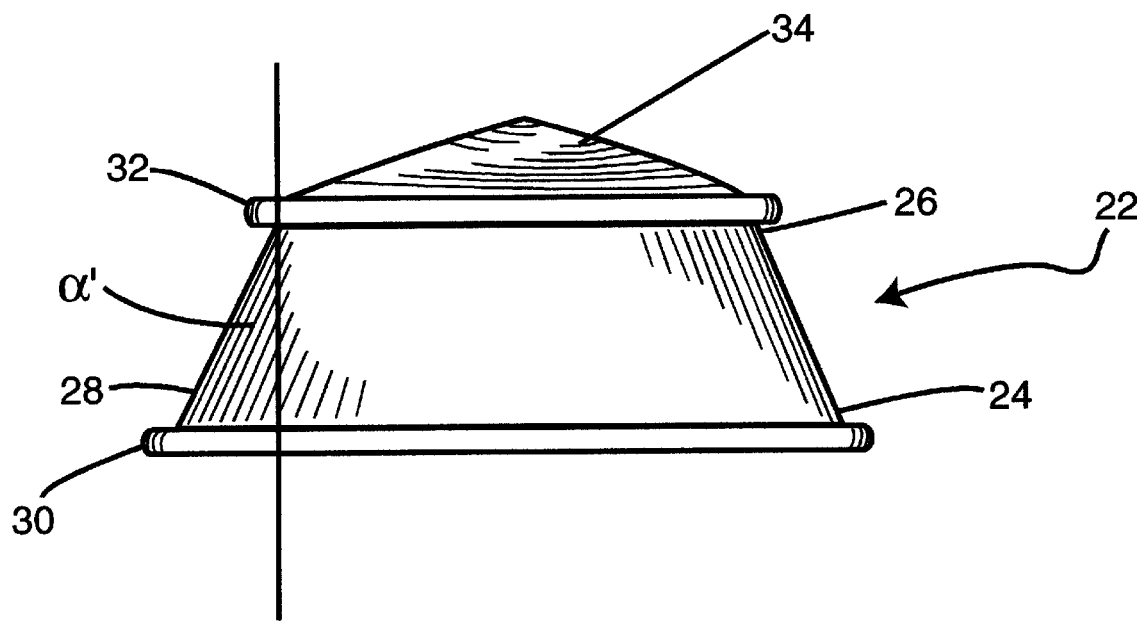
FIG. 3 is a perspective view of the tapered plunger wherein the angle of taper is exaggerated for illustration.

FIG. 3 is a perspective view of a typical tapered plunger of the present invention, generally designated with the numeral 22, showing the taper angle $\alpha$ which essentially corresponds to the angle $\alpha$ referred to in the description of the tapered syringe barrel.

The tapered plunger comprises:
proximal end 24;
distal end 26;
tapered cylindrical side wall 28 extending from the proximal end to the distal end;
an annular rim 30 extending away from the tapered cylindrical side wall at the proximal end;
an annular rim 32 extending away from the cylindrical side wall at the distal end, said annular rim 32 is being of smaller dimensions than said annular rim 30; and
a generally conical portion 34 extending vertically from the distal end of the tapered plunger.

The elastomeric tapered plunger 22 is slidably positioned in tapered syringe barrel 10. The taper angle $\alpha$ of the syringe barrel closely approximates taper angle $\alpha'$ of the plunger to ensure against leakage when the plunger is moved in the barrel in the proximal or distal direction.

In order to reduce the breakaway and running forces when reciprocating the plunger in the barrel, the elastomeric material used to fabricate the plunger should have a core set of no more than 20%. Most preferably, the elastomeric material will have a core set range of from about 10% to about 15%.

The plunger is supported by a plunger rod tip at the distal end of a plunger rod (not shown). The plunger rod tip and the plunger rod may be integral with each other, or the plunger rod tip and the plunger rod being of separate pieces are threaded together. In either case, the plunger rod tip is threaded into the plunger for support thereof.

Figure 4:
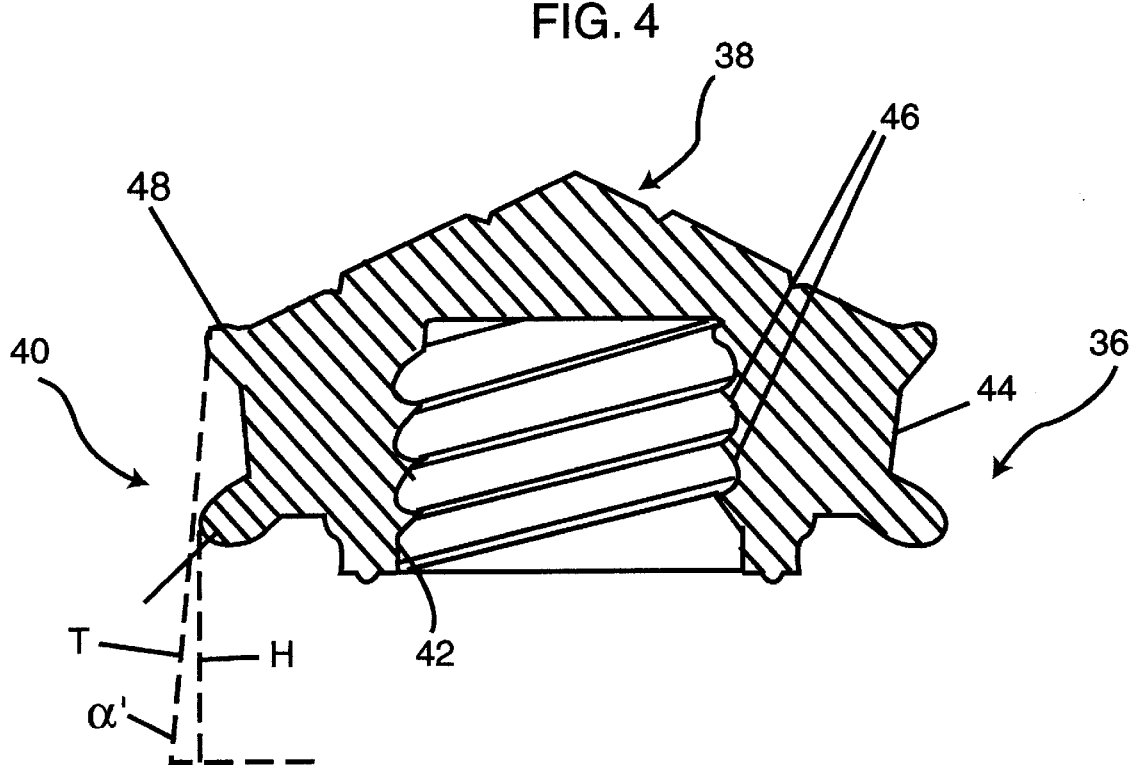
FIG. 4 is a cross-section of a further embodiment of the tapered plunger designed for use with a plunger rod having thread means thereon.

FIG. 4 shows a cross-section of a further embodiment of the tapered plunger of the present invention 36 for use with a plunger rod having a plunger rod tip with male thread thereon. The plunger comprises: a top conical portion generally designated at 38; a cylindrical side portion generally designated at 40; the cylindrical side portion having an inside wall 42 and an outside wall 44. The inside wall is provided with female threads 46 for engagement with a plunger rod tip having male threads thereon. The outside wall is provided with distal rim 48 and proximal rim 50, both of which extend away from the outside wall in a generally horizontal direction. Distal rim 48 is smaller than proximal rim 50 providing for the required taper configuration. Line T drawn tangent to proximal rim 50 and distal rim 48 illustrates the tapered angle a with respect to horizontal line H.

Figure 5:
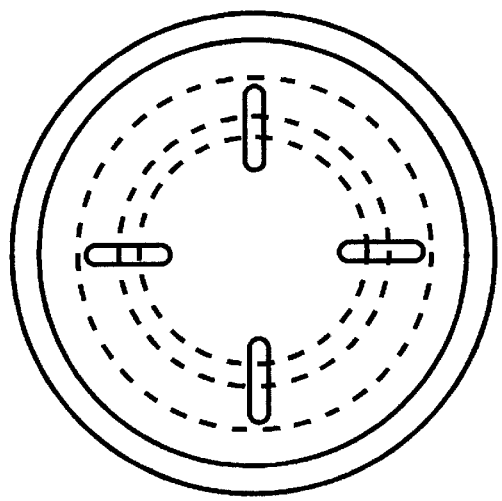
FIG. 5 is a top plan view of the plunger shown in FIG. 4.

FIG. 5 shows the top plan view of the plunger shown in FIG. 4.

Figure 6:
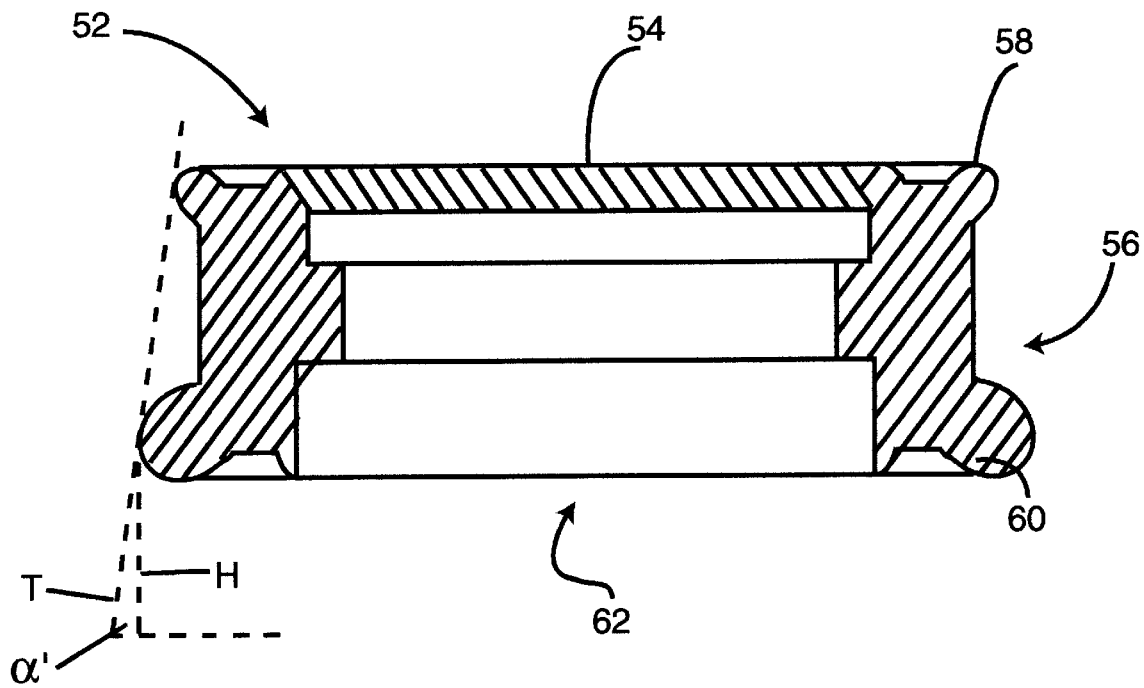
FIG. 6 is a cross-section of still a further embodiment of the tapered plunger having a horizontal top portion which interfaces with the content of the syringe barrel.

FIG. 6 shows a cross-section of still a further embodiment of the plunger of the present invention generally designated with the numeral 52 comprising a horizontal or flat top portion 54 and a side portion generally designated at 56.

Side portion 56 comprises distal rim 58 at the distal end of the plunger, and proximal rim 60 at the proximal end of the plunger. Distal rim 58 is smaller than proximal rim 60 providing for the required taper configuration. Line T drawn tangent to proximal rim 60 and distal rim 58 illustrates tapered angle $\alpha'$ with respect to horizontal line H. The plunger is positioned on a plunger rod tip generally designated by the numeral 62.

Figure 7:
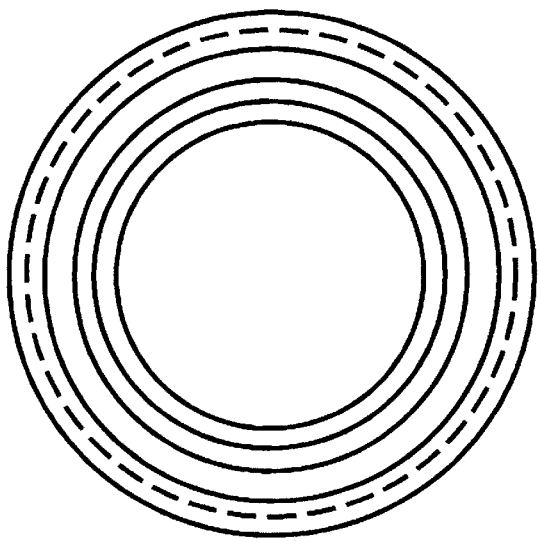
FIG. 7 is a top plan view of the plunger shown in FIG. 6.

FIG. 7 shows a top plan view of the plunger shown in FIG. 6.

Figure 8:
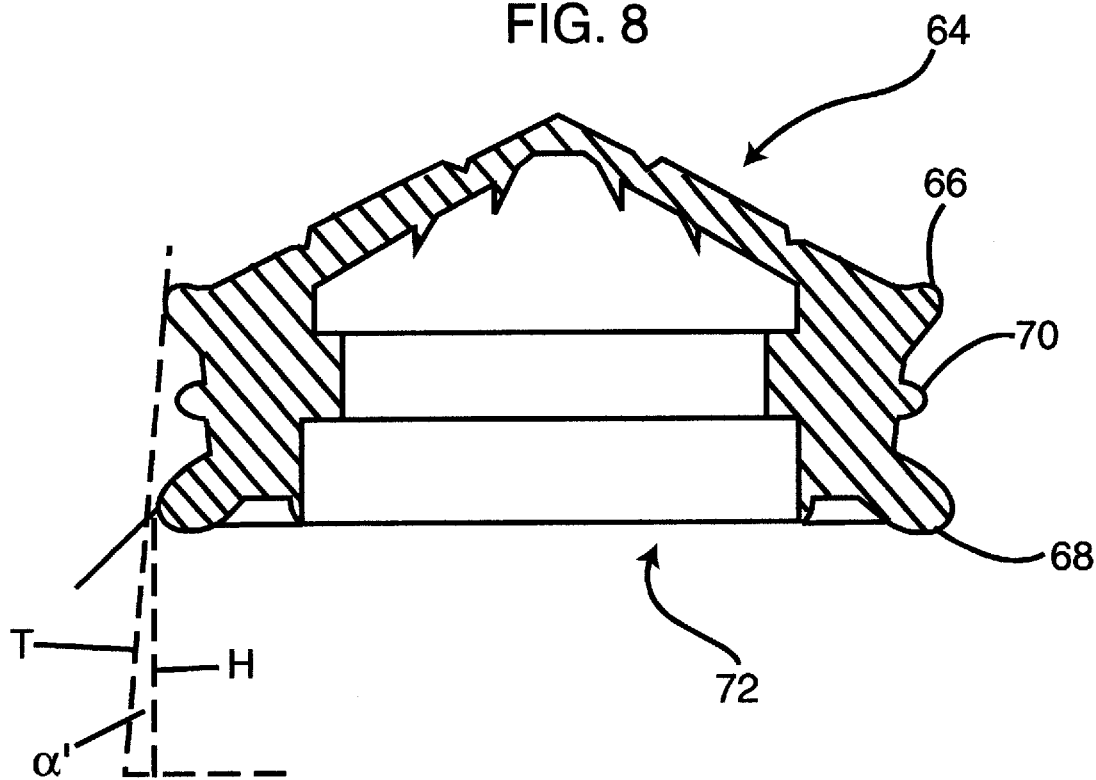
FIG. 8 is a cross-section of still another embodiment of a tapered plunger positioned on a plunger rod tip.

FIG. 8 shows a cross-section of sill another embodiment of the plunger of the present invention generally designated by the numeral 64 comprising:

a distal rim 66 oriented in a distal direction;

a proximal rim 68 oriented in a proximal direction; and a center rim 70 oriented horizontally toward the inside wall of a syringe barrel. Distal rim 66 is the smallest, proximal rim 68 is the largest, and center rim 70 has a size between distal and proximal rims. The three rims are aligned to provide for the required taper configuration. Line T drawn tangent to the rims illustrates the tapered angle $\alpha$ with respect to the horizontal line H. The plunger is positioned on a plunger rod tip generally designated at 72.

Figure 9:
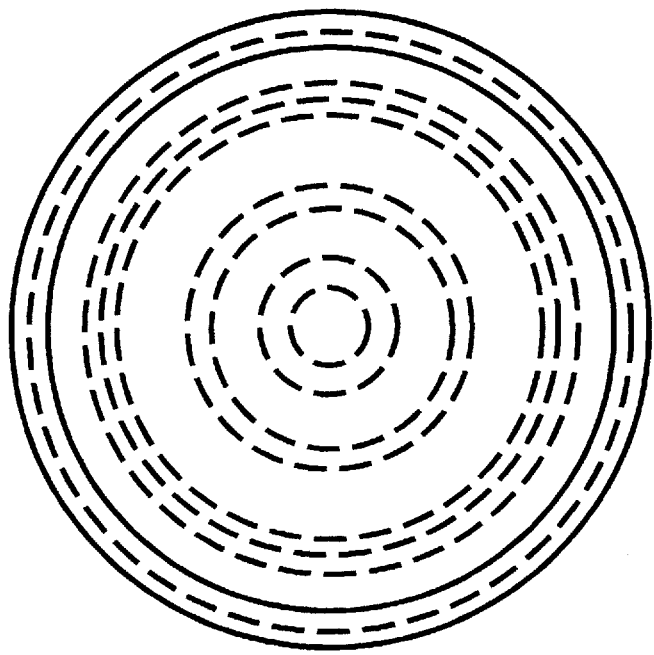
FIG. 9 is a top plan view of the tapered plunger shown in FIG. 8.

FIG. 9 is a top plan view of the plunger shown in FIG. 8.

Figure 10:
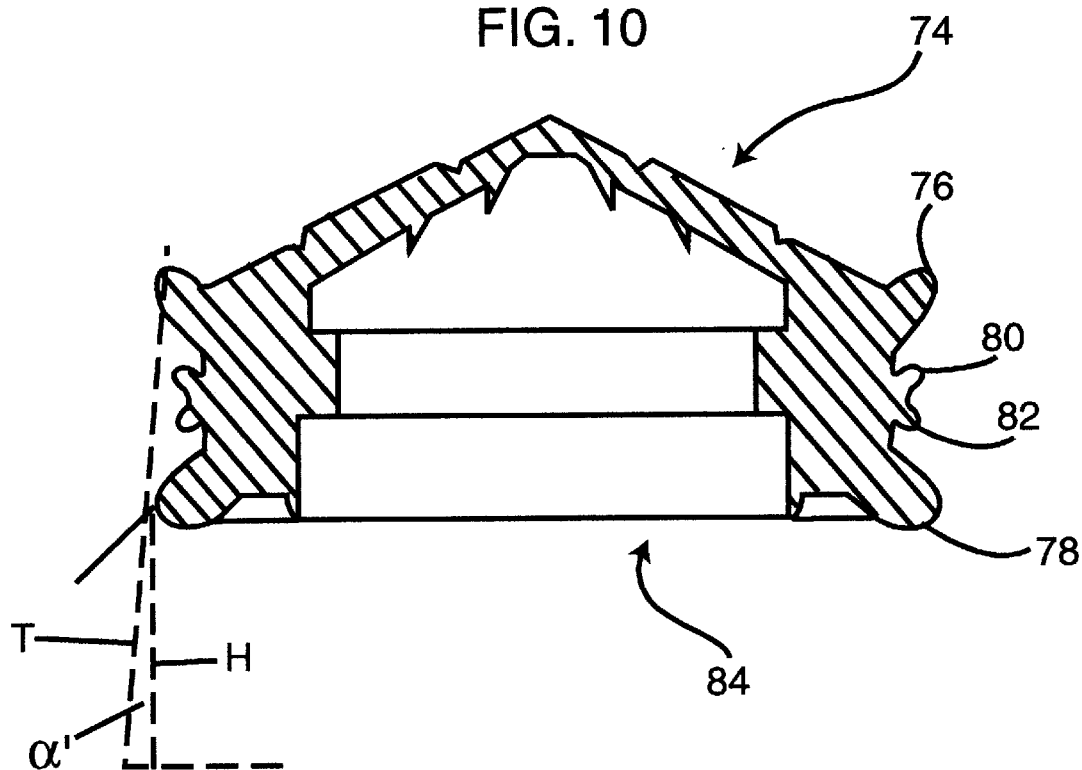
FIG. 10 is a cross-section of still a further embodiment of the tapered plunger positioned on a plunger rod tip.

FIG. 10 shows a cross-section of still another embodiment of the plunger of the present invention generally designated by the numeral 74 comprising:

a distal rim 76 oriented in the distal direction;

a proximal rim 78 oriented in the proximal direction; and two center rims 80 and 82, one oriented in the distal direction while the other is oriented in the proximal direction.

Distal rim 76 is smallest, proximal rim 78 is the largest and center rims 80 and 82 have a size which is intermediate between the distal rim and proximal rim. The four rims are aligned to provide for the required taper configuration. Line T drawn tangent to the rims illustrates the tapered angle $\alpha$ with respect to the horizontal line H. The plunger is positioned on a plunger rod tip generally designated at 84.

Figure 11:
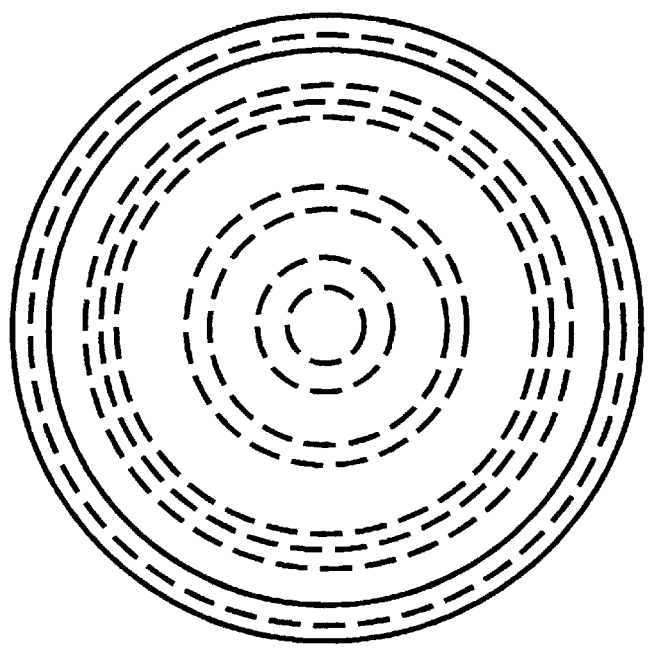
FIG. 11 is a top plan view of the tapered plunger shown in FIG. 10.

FIG. 11 is a top plan view of the plunger shown in FIG. 10.

The present invention embodied in the combination of a tapered syringe barrel and a tapered plunger positioned in the tapered syringe barrel with the specified criteria therein provide a consistent pressure at the plunger-to-barrel contact points and reduces operating forces in the syringe while maintaining fluid integrity under use.

| PARTS LIST | |
|---|---|
| Syringe barrel (generally designated) | 10 |
| Inside wall of syringe barrel | 12 |
| Tapered cylindrical chamber defined by inside wall | 13 |
| Proximal end of syringe barrel | 14 |
| Distal end of syringe barrel | 16 |
| Tip of syringe barrel having a bore therethrough | 18 |
| Angle of taper of the inside wall of syringe barrel | $\alpha$ |
| Outside wall of syringe barrel | 20 |
| Tapered plunger, generally designated | 22 |
| Angle of taper of cylindrical side wall | $\alpha'$ |
| Proximal end of plunger | 24 |
| Distal end of plunger | 26 |
| Tapered cylindrical side wall of plunger | 28 |
| Annular rim at the proximal end | 30 |
| Annular rim at the distal end | 32 |
| Conical portion of plunger | 34 |
| Plunger in a further embodiment | 36 |
| Top conical portion of plunger | 38 |
| Cylindrical side portion of plunger, generally designated | 40 |
| Inside wall of plunger | 42 |
| Outside wall of plunger | 44 |
| Female threads on inside wall of plunger | 46 |
| Distal rim of plunger | 48 |
| Proximal rim of plunger | 50 |
| Plunger in a further embodiment, generally designated | 52 |
| Horizontal top portion of plunger | 54 |
| Side portion of plunger, generally designated | 56 |
| Distal rim of plunger | 58 |
| Proximal rim of plunger | 60 |
| Plunger rod tip, generally designated | 62 |
| Plunger in a further embodiment, generally designated | 64 |
| Distal rim of plunger | 66 |
| Proximal rim of plunger | 68 |
| Center rim of plunger | 70 |
| Plunger rod tip | 72 |
| Plunger | 74 |
| Distal rim of plunger | 76 |
| Proximal rim of plunger | 78 |
| Center rims of plunger | 80 & 82 |
| Plunger rod tip, generally designated | 84 |

Various modifications of the present invention disclosed will become apparent. This invention is intended to include such modifications to be limited only by the scope of the claims.

What is claimed is:

1. A syringe designed for injecting a medical fluid into a site or withdrawing a medical fluid from a site comprising:

(a) a syringe barrel of polymeric material having a proximal end, a distal end;

an inner surface defining a tapered cylindrical chamber projecting from the proximal end towards the distal end for the containment of a medical fluid therein;

said distal end terminating in a tip having a bore therethrough for receiving an injection needle or a connector with a tubing conduit;

said proximal end is adapted for slidably receiving a plunger for reciprocating movement in said tapered cylindrical chamber;

(b) an elastomeric plunger supported by a rigid or semi-rigid plunger rod tip, having a proximal end and a distal end;

a tapered elastomeric body extending from said proximal end to said distal end, wherein said cylindrical chamber of said syringe barrel, and said elastomeric plunger having a taper of at least $\frac{1}{8}°$.

2. The syringe of claim 1 wherein said cylindrical chamber has a taper of at least 0.020 inches variation from the proximal end to the distal end thereof.

3. The syringe of claim 1 wherein said plunger has a taper of at least 0.020 inches variation from the proximal end to the distal end thereof.

4. The syringe of claim 1 wherein said tapered elastomeric body has a core set of about 20%.

5. The syringe of claim 1 wherein said elastomeric body has a core set of from about 10% to about 15%.

6. The syringe of claim 1 wherein said elastomeric body comprises an elastomer selected from the group consisting of butyl rubbers, polyisoprene, EPDM and natural rubbers.

7. The syringe of claim 1 wherein said syringe barrel is made of an inert gas impermeable polymeric material selected from the group consisting of polyethylene, polypropylene, polycarbonate, polymethylpentene, cyclic olefin copolymers, polystyrene, acrylic polymers and methacrylic polymers.

8. The syringe of claim 1 wherein said tapered elastomeric body further comprises:

an elastomeric proximal rim and an elastomeric distal rim projecting horizontally from said tapered elastomeric body of said tapered cylindrical chamber.

9. The syringe of claim 1 wherein said elastomeric plunger comprises:

an inside wall having female threads thereon for engagement with a plunger rod tip;

an outside wall having a proximal rim and a distal rim thereon projecting horizontally from said outside wall for interfacing said inner surface of said tapered cylindrical chamber.

10. The syringe of claim 1 wherein said elastomeric plunger comprises:

an outside wall having a proximal rim, a distal rim and a center rim thereon projecting away from said outside wall for interfacing said inner surface of said tapered cylindrical chamber.

11. The syringe of claim 1 wherein said elastomeric plunger comprises:

an outside wall having a proximal rim, a distal rim, and two center rims thereon projecting away from said outside wall for interfacing said inner surface of said tapered cylindrical chamber.

* * * * *